United States Patent
Yarmush et al.

(10) Patent No.: US 11,590,247 B2
(45) Date of Patent: Feb. 28, 2023

(54) SYSTEM AND METHOD FOR ELECTRICAL CONTROL OF BACTERIA

(71) Applicant: THE GENERAL HOSPITAL CORPORATION, Boston, MA (US)

(72) Inventors: Martin L. Yarmush, Boston, MA (US); William G. Austen, Weston, MA (US); Alexander Goldberg, Boston, MA (US); Saiqa I. Khan, Agawam, MA (US)

(73) Assignee: The General Hospital Corporation, Boston, MA (US)

( * ) Notice: Subject to any disclaimer, the term of this patent is extended or adjusted under 35 U.S.C. 154(b) by 265 days.

(21) Appl. No.: 16/882,102

(22) Filed: May 22, 2020

(65) Prior Publication Data

US 2020/0282088 A1 Sep. 10, 2020

Related U.S. Application Data

(63) Continuation of application No. 15/754,439, filed as application No. PCT/US2016/048684 on Aug. 25, 2016, now Pat. No. 10,660,979.

(Continued)

(51) Int. Cl.
| | |
|---|---|
| A61L 2/00 | (2006.01) |
| B01J 19/08 | (2006.01) |
| A61N 1/30 | (2006.01) |
| A61M 1/00 | (2006.01) |
| C25B 5/00 | (2006.01) |

(Continued)

(52) U.S. Cl.
CPC ........... *A61L 2/03* (2013.01); *A61B 18/00* (2013.01); *A61B 18/14* (2013.01); *C12N 13/00* (2013.01); *A61L 2202/24* (2013.01); *A61M 2025/0019* (2013.01); *A61N 1/20* (2013.01)

(58) Field of Classification Search
CPC . A61L 2/00; A61L 2/001; A61L 2/007; A61L 2/03; A61B 1/12; A61B 1/126; A61B 17/22
USPC ............... 422/22–23, 186.06; 204/156, 164; 604/19, 28–29, 109
See application file for complete search history.

(56) References Cited

U.S. PATENT DOCUMENTS 10,660,979 B2 * 5/2020 Yarmush ................... A61L 2/03
2012/0253125 A1 10/2012 Slenker et al.
(Continued)

FOREIGN PATENT DOCUMENTS

WO 2015049267 A1 4/2015

OTHER PUBLICATIONS

PCT International Search Report and Written Opinion, PCT/US2016/048684, dated Oct. 28, 2016, 14 pages.
(Continued)

*Primary Examiner* — Monzer R Chorbaji
(74) *Attorney, Agent, or Firm* — Quarles & Brady LLP

(57) ABSTRACT

A system and method for controlling microbial growth on and in medical devices and implants, especially biofilm infections, involves using pulsed electric fields (PEF). To eradicate at least a portion of a biofilm on a medical implant, for example, 1500 volts can be applied through an electrode system, with pulse duration of 50 μs and pulse delivery frequency of 2 Hz. In the clinical setting, systemic microbial therapy can be combined with PEF to achieve a synergistic effect leading to improved eradication of infections.

7 Claims, 6 Drawing Sheets

Related U.S. Application Data

(60) Provisional application No. 62/212,133, filed on Aug. 31, 2015, provisional application No. 62/209,912, filed on Aug. 26, 2015.

(51) Int. Cl.

| | |
|---|---|
| A61L 2/03 | (2006.01) |
| A61B 18/00 | (2006.01) |
| A61B 18/14 | (2006.01) |
| C12N 13/00 | (2006.01) |
| A61M 25/00 | (2006.01) |
| A61N 1/20 | (2006.01) |

(56) References Cited

U.S. PATENT DOCUMENTS

| | | | | |
|---|---|---|---|---|
| 2013/0041238 A1* | 2/2013 | Joseph | ............... | A61N 1/205 |
| | | | | 600/323 |
| 2015/0044092 A1* | 2/2015 | Allman | ............... | A61L 31/126 |
| | | | | 428/458 |
| 2015/0080291 A1* | 3/2015 | Zhang | ............... | C07K 5/06086 |
| | | | | 548/338.1 |

OTHER PUBLICATIONS

Albino et al., Immediate, Multistaged Approach to Infected Synthetic Mesh: Outcomes after Abdominal Wall Reconstruction with Porcine Acellular Dermal Matrix, Annals of Plastic Surgery, 2015, 75(6):629-633.
Álvarez et al., Inactivation of Yersinia Enterocolitica by Pulsed Electric Fields, Food Microbiology, 2003, 20(6):691-700.
Baelo et al., Disassembling Bacterial Extracellular Matrix with DNase-Coated Nanoparticles to Enhance Antibiotic Delivery in Biofilm Infections, Journal of Controlled Release, 2015, 209:150-158.
Bjarnsholt, The Role of Bacterial Biofilms in Chronic Infections, APMIS, 2013, 121(Suppl. 136):1-51.
Blumrosen et al., Efficient Procedure and Methods to Determine Critical Electroporation Parameters, In 2014 IEEE 27th International Symposium on Computer-Based Medical Systems, pp. 314-318.
Breuing et al., Incisional Ventral Hernias: Review of the Literature and Recommendations Regarding the Grading and Technique of Repair, Surgery, 2010, 148(3):544-558.
Chen et al., Metal Nanobullets for Multidrug Resistant Bacteria and Biofilms, Advanced Drug Delivery Reviews, 2014, 78:88-104.
Chen et al., Biofilm Removal Caused by Chemical Treatments, Water Research, 2000, 34(17):4229-4233.
Costerton et al., Microbial Biofilms, Annual Review of Microbiology, 1995, 49(1):711-745.
Dai et al., Photodynamic Therapy for Methicillin-Resistant *Staphylococcus aureus* Infection in a Mouse Skin Abrasion Model, Lasers in Surgery and Medicine, 2010, 42(1):38-44.
Davies et al., A Fatty Acid Messenger is Responsible for Inducing Dispersion in Microbial Biofilms, Journal of Bacteriology, 2009, 191(5):1393-1403.
Fernand et al., Variable Electric Fields for High Throughput Electroporation Protocol Design in Curvilinear Coordinates, Biotechnology and Bioengineering, 2012, 109(8):2168-2171.
Golberg, Long-Term Listeria Monocytogenes Proliferation Control in Milk by Intermittently Delivered Pulsed Electric Fields, Implications for Food Security in the Low-Income Countries, Technology, 2015, 3(1):1-6.
Golberg et al., Eradication of Multidrug-Resistant A. baumannii in Burn Wounds by Antiseptic Pulsed Electric Field, Technology, 2014, 2(2):153-160.
Golberg, Pulsed Electric Fields for Burn Wound Disinfection in a Murine Model, Journal of Burn Care & Research, 2015, 36(1):7-13.
Golberg et al., The Use of Irreversible Electroporation in Food Preservation, In Irreversible Electroporation, 2010, pp. 273-312.
Golberg et al., Skin Rejuvenation with Non-Invasive Pulsed Electric Fields, Scientific Reports, 2015, 5(1):1-18.
Golberg et al., Towards Electroporation Based Treatment Planning Considering Electric Field Induced Muscle Contractions, Technology in Cancer Research & Treatment, 2012, 11(2):189-201.
Golberg et al., Nonthermal Irreversible Electroporation: Fundamentals, Applications, and Challenges, IEEE Transactions on Biomedical Engineering, 2013, 60(3):707-714.
Hamblin et al., Rapid Control of Wound Infections by Targeted Photodynamic Therapy Monitored by In Vivo Bioluminescence Imaging. Photochemistry and Photobiology, 2002, 75(1):51-57.
Hoiby, et al., Antibiotic Resistance of Bacterial Biofilms, International Journal of Antimicrobial Agents, 2010, 35(4):322-332.
Johansen et al., Enzymatic Removal and Disinfection of Bacterial Biofilms, Applied and Environmental Microbiology, 1997, 63(9):3724-3728.
Jolivet-Gougeon et al., Bacterial Hypermutation: Clinical Implications, Journal of Medical Microbiology, 2011, 60(5):563-573.
Manca et al., Treatment of Keloids and Hypertrophic Scars with Bleomycin and Electroporation, Plastic and Reconstructive Surgery, 2013, 132(4):621e-630e.
Markley et al., Protection by Vaccination Against Pseudomonas Infection after Thermal Injury, Journal of Bacteriology, 1968, 96(4):867-874.
Mir et al., Standard Operating Procedures of the Electrochemotherapy: Instructions for the Use of Bleomycin or Cisplatin Administered either Systemically or Locally and Electric Pulses Delivered by the Cliniporator(TM) by Means of Invasive or Non-Invasive Electrodes, European Journal of Cancer Supplements, 2006, 4(11):14-25.
Murtagh et al., Large-Scale Linearly Constrained Optimization, Mathematical Programming, 1978, 14(1):41-72.
Neal III et al., Successful Treatment of a Large Soft Tissue Sarcoma with Irreversible Electroporation, Journal of Clinical Oncology, 2011, 29(13):e372-e377.
Peleg et al., Estimating the Survival of Clostridium Botulinum Spores During Heat Treatments, Journal of Food Protection, 2000, 63(2):190-195.
Peleg et al., Modeling Microbial Survival During Exposure to a Lethal Agent with Varying Intensity, Critical Reviews in Food Science and Nutrition, 2000, 40(2):159-172.
Ragas et al., Photodynamic Inactivation of Acinetobacter Baumannii Using Phenothiazinium Dyes: In Vitro and In Vivo Studies, Lasers in Surgery and Medicine, 2010, 42(5):384-390.
Rocchetta et al., Validation of a Noninvasive, Real-Time Imaging Technology Using Bioluminescent *Escherichia coli* in the Neutropenic Mouse Thigh Model of Infection, Antimicrobial Agents and Chemotherapy, 2001, 45(1):129-137.
Rosenthal, Local and Systemic Therapy of Pseudomonas Septicemia in Burned Mice, Annals of Surgery, 1967, 165(1):97-103.
Sandt et al., Confocal Raman Microspectroscopy as a Tool for Studying the Chemical Heterogeneities of Biofilms in Situ, Journal of Applied Microbiology, 2007, 103(5):1808-1820.
Sersa et al., Vascular Disrupting Action of Electroporation and Electrochemotherapy with Bleomycin in Murine Sarcoma, British Journal of Cancer, 2008, 98(2):388-398.
Turakhia et al., Influence of a Calcium-Specific Chelant on Biofilm Removal, Applied and Environmental Microbiology, 1983, 46(5):1236-1238.
Vecchio et al., Antimicrobial Photodynamic Therapy with RLP068 Kills Methicillin-Resistant *Staphylococcus aureus* and Improves Wound Healing in a Mouse Model of Infected Skin Abrasion, Journal of Biophotonics, 2013, 6(9):733-742.
Weaver, Electroporation of Cells and Tissues, IEEE Transactions on Plasma Science, 2000, 28(1):24-33.
Xavier et al., Biofilm Control Strategies Based on Enzymic Disruption of the Extracellular Polymeric Substance Matrix-a Modeling Study, Microbiology, 2005, 151(12):3817-3832.
Yarmush et al., Electroporation-Based Technologies for Medicine: Principles, Applications, and Challenges, Annual Review of Biomedical Engineering, 2014, 16:295-320.

* cited by examiner

SYSTEM AND METHOD FOR ELECTRICAL CONTROL OF BACTERIA

CROSS-REFERENCE TO RELATED APPLICATIONS

This application is a continuation of U.S. application Ser. No. 15/754,439 filed Feb. 22, 2018 which is a U.S. National Phase of PCT/US16/48684 filed Aug. 25, 2016 which is based on, claims priority to, and incorporates herein by reference in their entirety, U.S. Application Ser. No. 62/212,133, filed Aug. 31, 2015, and entitled "Eradication of Biofilm with Pulsed Electric Fields," and U.S. Application Ser. No. 62/209,912, filed Aug. 26, 2015, and entitled "Eradication of Biofilm with Pulsed Electric Fields."

STATEMENT REGARDING FEDERALLY SPONSORED RESEARCH

This invention was made with government support under R01 AI050875 awarded by the National Institutes of Health. The government has certain rights in the invention.

FIELD OF THE INVENTION

This document concerns an invention relating generally to electrical control of non-planktonic microbial growth, and more specifically to disruption of bacterial growth and eradication of bacteria using pulsed electric fields.

BACKGROUND

Bacterial infections that exist as single independent cells are referred to as planktonic, and are generally treated with antibiotics depending on relatively fast and accurate diagnoses. In contrast, a biofilm is an accumulation of bacteria embedded in a polysaccharide matrix, which adheres to a biologic or non-biologic surface. The formation of biofilm is a significant medical problem, accounting for over eighty percent of microbial infections in the body. Examples include infections of indwelling catheters, cardiac implants, prosthetic heart valves, synthetic vascular grafts and stents, internal fixation devices, prostheses, synthetic mesh, tracheal and ventilator tubing, oral soft tissues, dental implants and teeth, middle ear, gastrointestinal tract, airway/lung tissue, eyes, urogenital tract, urinary tract prostheses, peritoneal membrane and peritoneal dialysis catheters, and percutaneous sutures. Bacteria within biofilms have increased resistance to antibiotics, even though these same bacteria are sensitive to antibiotics if grown under planktonic conditions. The matrix of extracellular polymeric substances (EPSs) has an essential role in defining the cohesiveness and other physical properties of these adherent microbial communities. Additionally, biofilm growth increases the opportunity for gene transfer between bacteria, therefore further perpetuating antibiotic resistance. Recent studies have shown that extracellular DNA, secreted by bacteria, prevent efficient drug delivery to the biofilms. Control of biofilm persistence and growth is thus problematic due to increased resistance to treatment with antibiotics as compared to planktonic cells.

Use of a synthetic mesh is currently the most common repair material used for reinforcement of ventral hernias. Mesh infection is an example of a type of implant infection in which surgical removal and debridement can result in significant morbidity for patients. Two million Americans undergo abdominal surgery annually with a postoperative incisional hernia rate of 10 to 23 percent. About 400,000 ventral hernia repairs are performed each year in the United States alone, with reported hernia recurrences in 40 to 50 percent of cases. Synthetic mesh reinforces hernia repairs and has been shown to decrease recurrences compared to primary repair alone. However, morbidities related to mesh infection can limit efficacy. Reported mesh infection rates range from 4 to 16 percent. Known mesh complications include infection requiring prolonged antibiotic coverage, surgical debridements, and mesh explanation. Postoperative mesh infections requiring debridement and mesh explanation continue to be devastating problems for patients, and a reconstructive challenge for surgeons.

Multiple pathways may lead to infection of synthetic mesh. Patients may have an acute postoperative mesh infection, or dehiscence of the wound may expose the mesh, leading to colonization and infection of the prosthesis. Reoperation through synthetic mesh may also lead to infection. Additionally, seromas that develop may become infected, leading to subsequent contamination and removal of the prosthesis. The bacteria that commonly infect mesh are methicillin-resistant *Staphylococcus aureus* (MRSA), *Enterococcus faecalis, Escherichia coli, Proteus mirabilis, Prevotella bivia*, and *Pseudomonas aeruginosa*. Antibiotics alone are not an effective treatment for mesh infections.

Techniques for promoting biofilm detachment with chemical and enzymatic agents that attack the EPS matrix have been investigated with variable and overall disappointing results. Because there is no effective treatment for biofilm infections, the gold standard treatment is mechanical removal of the infected material and/or tissue. But mechanical removal is not always possible without risk of serious complications. If the biofilm infected material cannot be removed, the patient is placed on chronic suppressive antibiotics, therefore requiring several different antibiotics at high doses for an extended period of time. This may induce further resistance, tolerance, and eventually chronic infection.

What is needed is a non-antibiotic based intervention that addresses biofilm infections and reduces emerging microbial resistance to multiple drugs.

SUMMARY

The present disclosure provides devices and methods for disinfecting medical devices and implants using pulsed electric fields (PEF). High-voltage, microsecond pulsed electric fields create non-thermal pores in cell membranes of microbes via irreversible electroporation, causing non-thermal permanent damage to cell membranes. With sufficient electric field strength, biofilm disruption and microbial eradication can be achieved without damage to the medical device on which the microbes and biofilm are found. In one embodiment, a disinfection system may be provided with suitable electrodes that can be positioned at the medical device or implant to be disinfected. Alternatively or additionally, a medical device can be brought to the system for disinfection, such as by being positioned in a device receptacle configured to apply PEF to devices placed inside. A suitable protocol, which specifies such parameters as voltage, pulse duration, and pulse frequency, can be selected before or after the electrode or device is in position.

The protocol to be used may be selected based in part on the type of microbe, the device or implant to be disinfected, and/or the surface area that is infected. For example, a biofilm-infected mesh, such as a synthetic prolene mesh infected with *Pseudomonas aeruginosa*, can be treated with pulsed electric fields using concentric electrodes or other electrode system. A protocol of 1500 volts applied via a central electrode, with a pulse duration of 50 µs, and a pulse delivery frequency of 2 Hz, can be used. The critical electric field strength (Ecr) needed to eradicate 100-80% of bacteria in such a treated area is expected to be between about 100 and 150 V/mm when 300 pulses are applied, and between about 225 and 250 V/mm when 150 pulses are applied. The area at which 100-80% of bacteria is eradicated is about 40 and 60 mm$^2$ for 300 pulses, and about 12 to 15 mm$^2$ for 150 pulses. In the clinical setting, combining systemic antimicrobial therapy with PEF could yield a synergistic effect leading to improved eradication of microbes found in implant infections.

Such applications of PEF to microbes may be used in treatment of biofilm infections without the morbidity and complications associated with removal of infected material and chronic high-dose antibiotics. As a non-antibiotic based intervention, this approach is useful against biofilm infections while reducing emerging bacterial resistance to drugs. Such use of PEF can help eradicate biofilm on implanted medical devices in a non-chemical, non-thermal manner. Moreover, the disclosed PEF approach can avoid costly treatments such as reoperation to remove infected material, and reduce subsequent morbidity, recurrence, life-long high dose antibiotic regimens, and decreased quality of life.

The foregoing and other aspects and advantages of the invention will appear from the following description. In the description, reference is made to the accompanying drawings which form a part hereof, and in which there is shown by way of illustration one or more preferred embodiments of the invention. Such embodiments do not necessarily represent the full scope of the invention, however, and reference is made therefore to the claims for interpreting the scope of the invention.

BRIEF DESCRIPTION OF THE DRAWINGS

In FIG. 5A, an untreated infected mesh demonstrated thick biofilm wedged into mesh interstices (left image). Dense bacteria revealed production of exopolysaccharide (right image). In FIG. 5, after treatment with PEF using concentric electrodes, the biofilm has been disrupted and debris is left behind (left image). The few remaining scant rods displayed abnormal morphology, and exopolysaccharide was not visible (right image).

FIG. 6A shows bioluminescent values measured from N=3 mesh pieces per group, demonstrating the average of all treatments per pulse group compared to the theoretical Weibull distribution as a function of the electric field strength. Survival rate decreases as the number of pulses and electric field strength increase. FIG. 6B shows an ANOVA test revealing that the p-value between the different conditions (pulse number) is 0.000056, which indicates that treatment efficacy directly correlates to number of pulses delivered. Treatment efficiency is defined by the percent of eradicated bacteria, as measured by the percent of bioluminescence reduction at the specific location.

DETAILED DESCRIPTION

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures depict selected embodiments and are not intended to limit the scope of embodiments of the invention. Skilled artisans will recognize the examples provided herein have many useful alternatives that fall within the scope of embodiments of the invention.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, diodes, look-up tables, etc., which may carry out a variety of functions under the control of one or more microprocessors or other control devices. Other embodiments may employ program code, or code in combination with other circuit components. It should also be appreciated that certain components and functions may be shared and/or shuffled between blocks and among blocks in different embodiments of the invention, as deemed suitable. For example, the role of a processing unit may range from giving a command to a generator to generate pulses according to a self-directed protocol, without coordination of the generation by the processing unit, or it may take a more active role in the steps involved in implementing a particular generation protocol.

Figure 1:
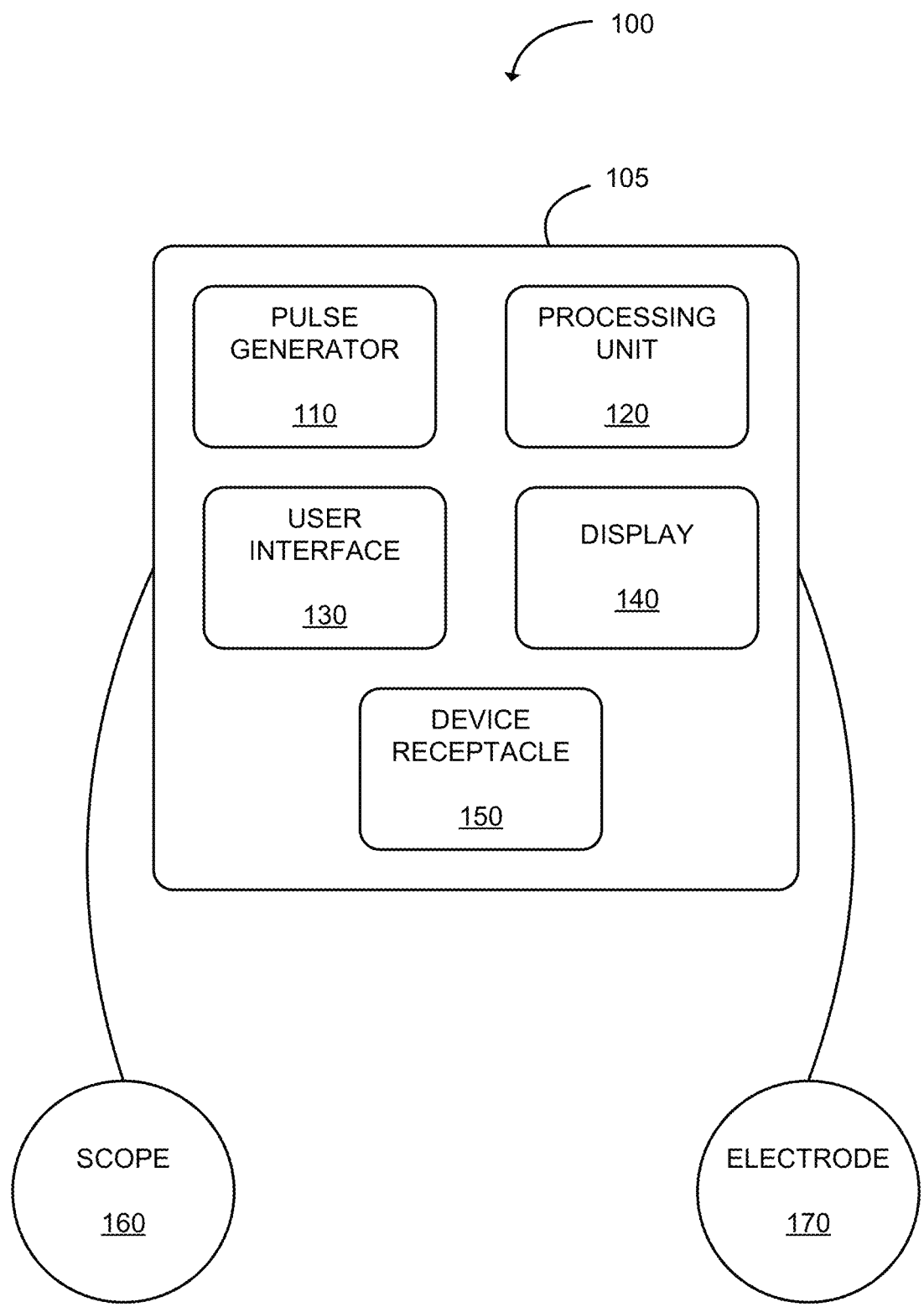
FIG. 1 is an exemplary biofilm eradication system with a pulse generator able to generate electric fields via an electrode, and/or to disinfect medical devices received in a device receptacle. A scope may optionally interface with the system to facilitate visual observation, such as a laparoscope that could be used in surgery.

Referring to FIG. 1, an exemplary disinfection system 100 may include a controller 105 having a pulse generator 110 for generation of pulsed electric fields (PEF) to be applied to biofilm infections. A processing unit 120 controls the pulse generator 110 as well as other components and functions of the system 100. A user interface 130 allows a user to input information and make selections via, for example, one or more of a keyboard, computer mouse, and touchscreen. A display 140 serves as an output device for presentation of information, and may incorporate any suitable technology (including without limitation liquid crystal display, light emitting diode, etc.). In certain embodiments, a device receptacle 150 may be provided as a space in which the device to be disinfected can be placed. A scope 160 may optionally be included to allow a user (such as a surgeon) to visually locate a medical device or implant (or a portion thereof) to be disinfected, or to more easily identify the microbes in the biofilm to be eradicated.

An electrode system 170 may be provided for disinfecting devices that are not easily transported to the system 100 for placement in the receptacle 150, such as devices implanted in a patient. The system 100 may have both the ability to apply pulsed electric fields externally via an extendible electrode system 170, as well as "internally" via the device receptacle 150, which may be an enclosure with one or more of its own electrodes for applying pulsed electric fields to devices placed in the receptacle 150. An exemplary electrode system may include a ring electrode concentric with a needle electrode, the two secured to each other via a non-conducting material, or an array of needles arranged to apply pulsed electric fields as desired. The needles in such an array can be arranged linearly or non-linearly, and the electrodes (rings, needles, etc.) may be sized and spaced so as to accommodate (for example) the sizes and shapes of devices to be disinfected, the magnitude of the pulses to be applied, the area to be disinfected, and/or the surroundings of the device (such as location in the body and the size of openings through which the electrode system must pass). Once a device is positioned in the receptacle 150, the electrodes may be moved into place relative to the device by, for example, a sliding or pivoting motion. To accommodate devices with different shapes and sizes, the electrode positions may be further adjustable to allow for fine-tuning after they have slid or pivoted into place. A slidable/pivotable cover may also be provided to help contain the device in the receptacle 150 and keep contaminants out during disinfection. The electrodes may be secured to the cover, such that "closing" the receptacle concurrently or automatically slides/pivots the electrodes into position with respect to the device.

The processing unit 120 includes a processor, one or more memory modules, and instructions in the form of software (which can be loaded into the memory), firmware, hardware, or any combination thereof. The components of the processing unit 120 are involved in coordination and implementation of the functionality of the system 100 by, for example, interfacing with the pulse generator 110 to control the generation of pulsed electric fields, the user interface 130 to receive inputs, the display 140 to provide outputs, and the scope 160 to receive images. The processing unit 120 may also serve as an intermediary between, for example, the pulse generator 110 and the electrode 170 (to, e.g., initiate application of pulsed electric fields), the scope 160 and the display 140 (to, e.g., process images to be displayed), and the user interface and the device receptacle 150 (to, e.g., initiate disinfection).

Figure 2:
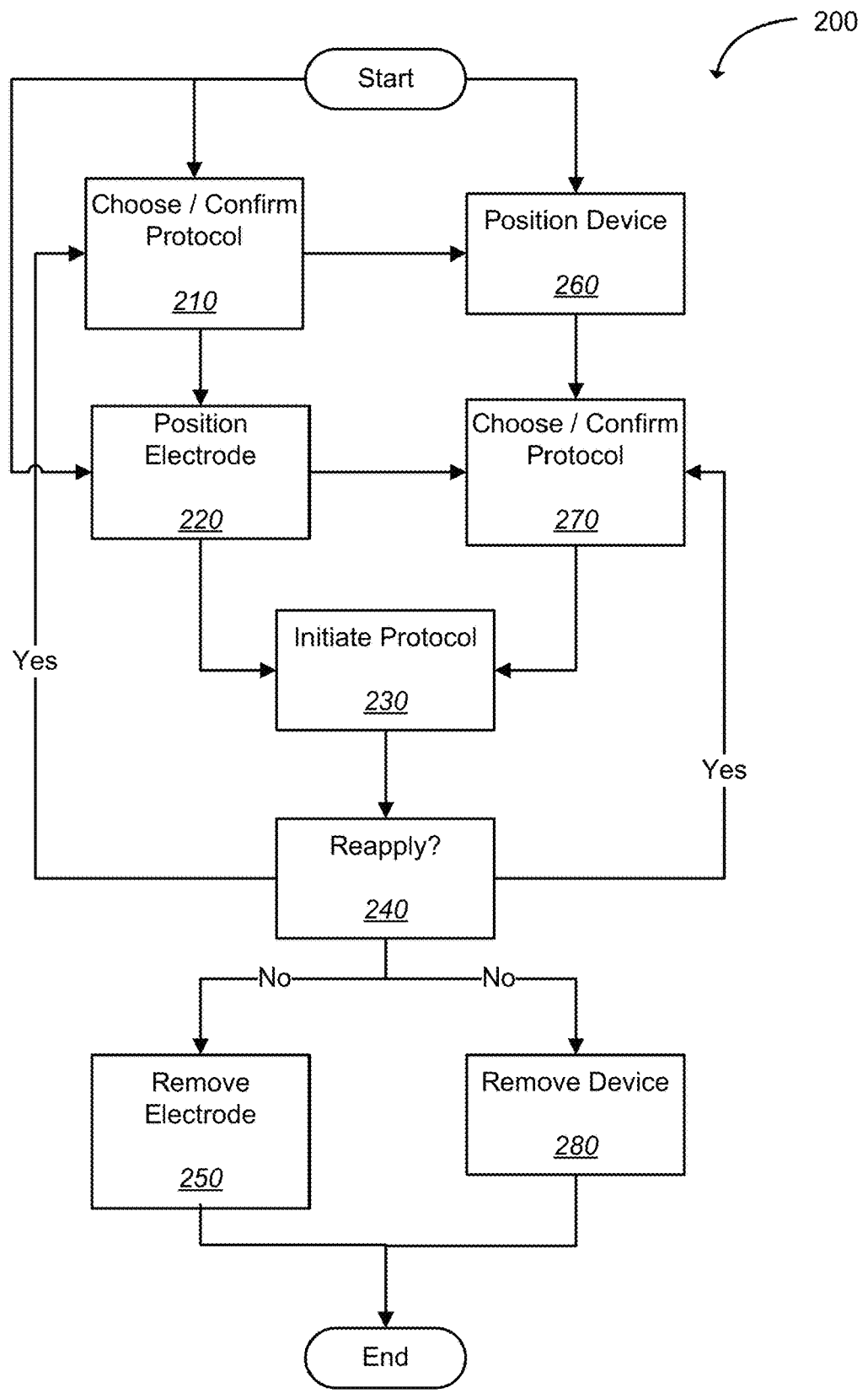
FIG. 2 is an exemplary process of disinfecting a medical device or an implant, involving selection of a protocol to be used and positioning of the medical device or implant relative to the applicator to be used to apply pulsed electric fields

Referring to FIG. 2, an exemplary process 200 of using the disinfection system 100 may begin by having a user choose a protocol 210 to be applied to an infection. The electrode may be positioned 220 at the device or implant to be disinfected, and the protocol may be initiated 230 to apply the selected pulsed electric field protocol. If pulsed electric fields are to be applied once more 240, the user may choose/confirm a new protocol (or use of the same protocol) 210. If no reapplication is desired 240, the electrode may be retracted and moved away from the medical device 250. Alternatively, the process may involve positioning the device to be disinfected 260 in the device receptacle 150 of the disinfection system 100. That is, instead of using electrode 170 to bring the pulsed electric fields to a device, the device can be brought to the system 100 to receive the pulsed electric field. A protocol may be selected before (210) or after (270) the device is positioned 260. (Similarly, the protocol may be selected 270 after positioning of the electrode 220.) Once the device is positioned and the protocol selected and/or confirmed, the process continues as before, with initiation of the protocol 230. If protocol is to be reapplied 240, the user may select a new protocol (or use the same protocol) 270 for initiation of pulsing 230. If pulsed electric fields are not to be reapplied, the device can be removed 280 from the device receptacle 150.

Figure 3:
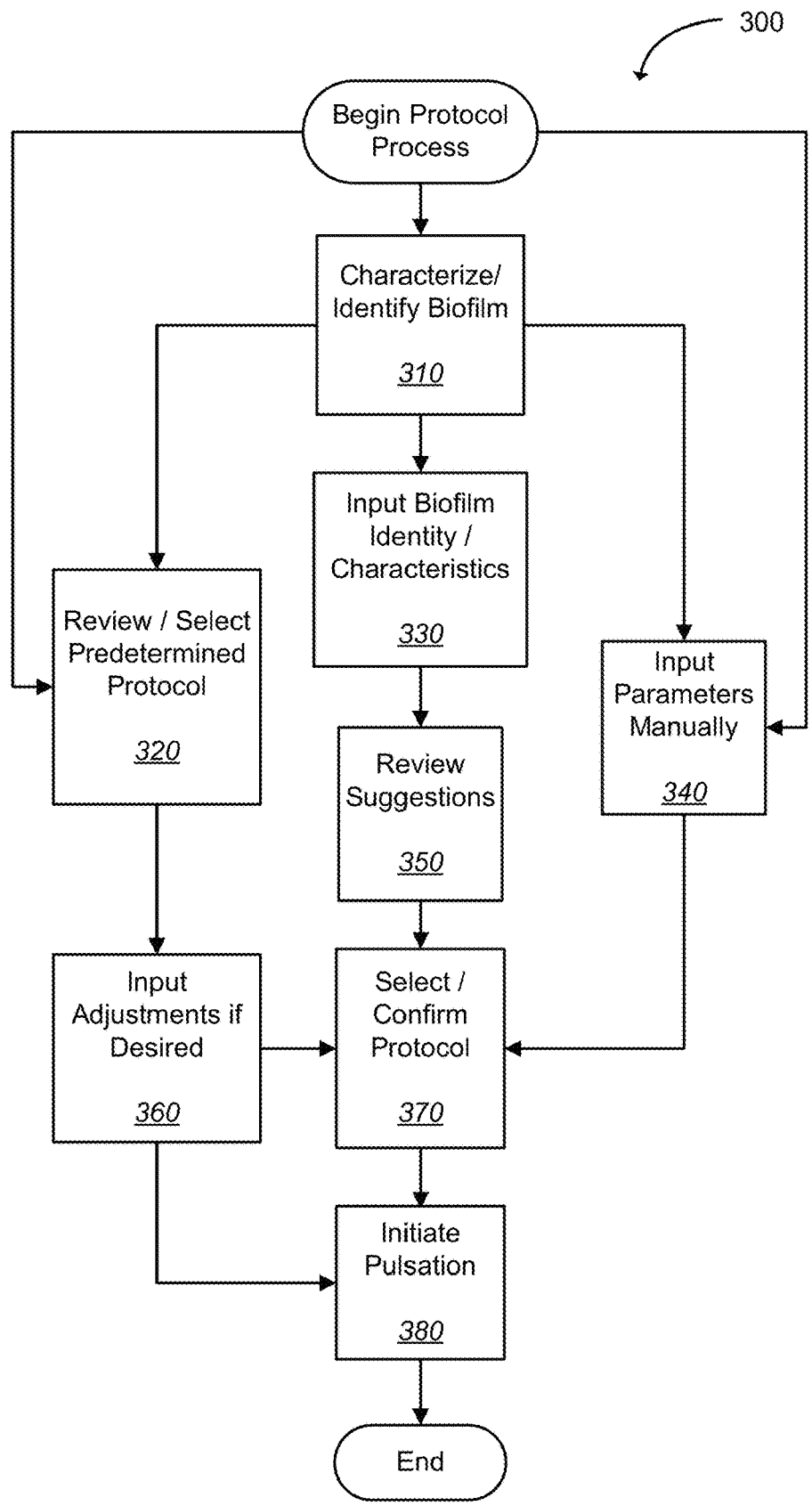
FIG. 3 is an exemplary protocol process referenced in FIG. 2, involving selection of an available protocol among a set of predetermined/preselected protocols, automated selection based on information about the infection, or manual input of the parameters for a user-defined protocol for the pulsed electric fields.

An exemplary process 300 for determining which protocol is to be applied is represented in FIG. 3. A user may begin by characterizing the biofilm 310, which may include identification of the microbial species and/or estimation of the size of the biofilm (e.g., the surface area covered by the biofilm or its thickness). Characterization and identification could be accomplished via one or more approaches, such as staining, serological tests, phage typing, fatty acid profiling, flow cytometry, nucleic acid-based techniques, etc., or a combination thereof as deemed suitable depending on whether a sample taken from the biofilm is available. It might be deemed sufficient to have a high-level classification of the microbe, or have more detail including identification of species and strain. Once the biofilm has been identified, a user may input the characteristics 330 into the system 100, and the system 100 may, based on the characteristics, propose or recommend one or more suitable protocols for review 350 via display 140. The user then may select/confirm the desired protocol 370, after which the pulsed electric fields may be applied 380.

In a less "automated" alternative process, once the biofilm has been characterized/identified 310, the user may review from among a set of predetermined/preselected protocols 320 suitable for multiple microbes/biofilms and select one of the predetermined/preselected protocols. The parameters for such predetermined protocols could be set such that they are suitable in multiple situations (e.g., expected to be effective for a set of devices and/or a group of microbes) based on prior experiments and experiences. Once a predetermined/preselected profile has been selected, the user may optionally wish to customize or otherwise adjust a subset of the parameters of the predetermined/preselected protocol, and such adjustments may be input 360 into the system 100 via user interface 130. The user may then be asked to confirm the modified protocol 370, if required, before initiating pulsation 380. It is noted that the process 300 may also begin by review and selection of predetermined/preselected protocols 320, without characterization and/or identification of the biofilm 310. The protocol may be adjusted/customized if desired 360 before initiating pulsation 380. In yet another alternative implementation of the process 300, the user may begin by manually entering the parameters of the protocol to be applied 340. Once the parameters have been confirmed 370, pulsation may begin 380.

Figure 4A:
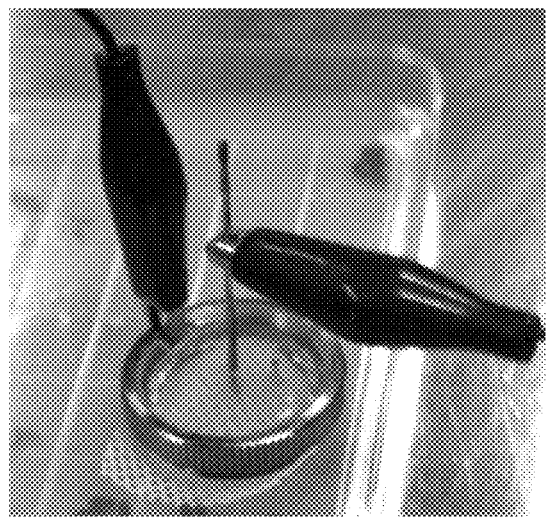
FIG. 4A shows concentric ring electrodes applied to infected mesh as part of evaluation of suitable protocols for use with various medical devices and biofilm infections.
Figure 4B:
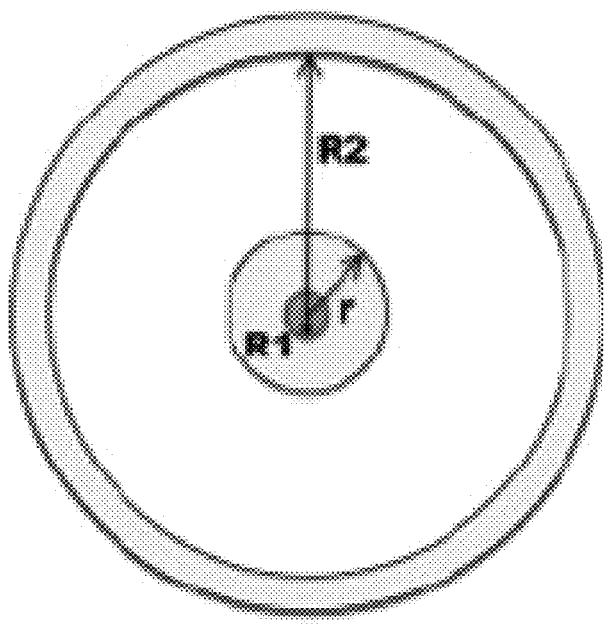
FIG. 4B represents the relative dimensions of such an exemplary electrode system for use in mathematical models applicable to pulsed electric field treatments, particularly with respect to Equation (1), discussed below.

Selection of an effective protocol—whether based on a recommendation of the disinfection system 100 (following characterization/identification 310), selection from among predetermined/preselected protocols, or a user-defined protocol—is influenced by such factors as the microbe (e.g., class, type, species, strain), infected area, etc. For example, disinfecting a nonabsorbable synthetic prolene mesh that is infected with the pathogenic Gram-negative bacterium *Pseudomonas aeruginosa* has been found to respond to certain electric field pulses when applied via concentric ring electroporation, which delivers a centrifugal gradient of disinfection from the center outwards to the periphery. The center of the mesh, where the needle is in direct contact (see FIG. 4A), receives the highest electric field strength. This electric field strength decreases in an outward direction from the center to the outer rim. For concentric ring electroporation, Equation (1) can be used to solve for the local electric field strength E(r) at any given radius (r). In the system of concentric electrodes, the field strength is a function of radius and applied voltage (V) according to Equation (1):

$$E(r, V) = \frac{V_1 - V_2}{r \ln\left(\frac{R2}{R1}\right)} \quad (1)$$

where V1 is the voltage delivered through the central needle, V2 is the voltage at the external ring, r is the radial distance of each point inside the treatment area from the center, R1 is the radius of the needle, and R2 is the external ring radius (see FIG. 4B).

In one experiment, a sterile, nonabsorbable synthetic prolene mesh (Ethicon, Calif.) was infected with the pathogenic Gram-negative bacterium *Pseudomonas aeruginosa* that had been rendered bioluminescent. The *P. aeruginosa* strain employed was ATCC 19660 (strain 180). It can cause septicemia by intraperitoneal injection, and is pathogenic in mice with infected cutaneous burns. The bioluminescent variant (strain Xen 05) carried the integrated bacterial lux operon into its chromosomes for stable bacterial luciferase expression, which allowed them to be used for bioluminescent imaging. A colony of bioluminescent *Pseudomonas aeruginosa* was then placed in a 50 mL falcon tube with prolene mesh and 30 mL of brain heart infusion broth (BHI). This was agitated on a shaker at 180 rpm for 30 minutes at room temperature and then moved to a C24 Incubator Shaker (Brunswick Scientific) at 37° C. with agitation at 100 rpm for three days. After three days, the infected mesh was placed on sterile agar plates and incubated overnight at 37° C., 5% $CO_2$.

Referring to FIG. 4A, to evaluate pulsed electric field disinfection of prolene mesh, an experimental set-up of concentric ring electroporation with a one-dimensional cylindrical system was used, with the diameter of the inner cylinder, represented by an 18-gauge steel needle, measuring 1 mm, and the outer cylinder measuring 22 mm in diameter. The needle was inserted through the center of the plastic in the middle of the brass ring forming two concentric cylindrical electrodes. Alligator clips were attached to the brass ring and the 18G needle. The system was placed on the mesh with the needle located at the center of the mesh. The clips were hooked up to a BTX 830 pulse generator (Harvard Apparatus Inc, Holliston Mass., USA). The PEF parameters tested were: 1500 Volts (V1), 0 Volts (V2); 100, 150, and 300 pulses, at 50 μs pulse length duration and 2 Hz frequency.

Figure 5A:
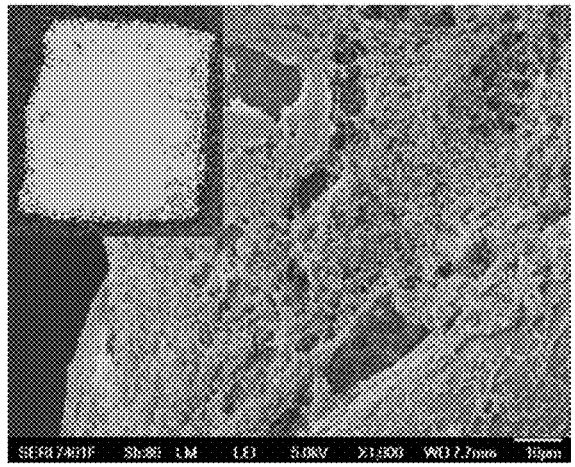
FIG. 5A shows bioluminescent images of infected mesh prior to treatment with pulsed electric fields.
Figure 5A:
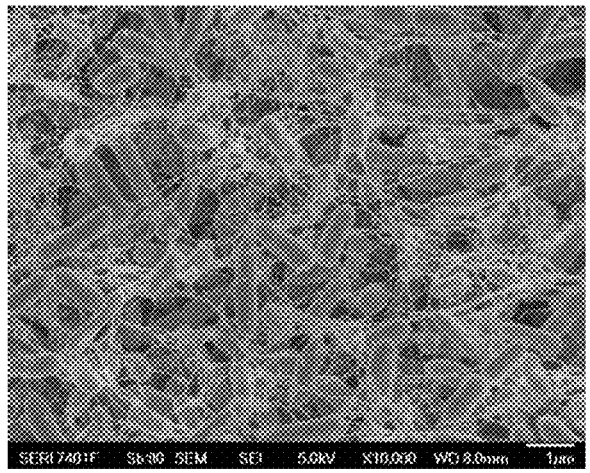
Figure 5B:
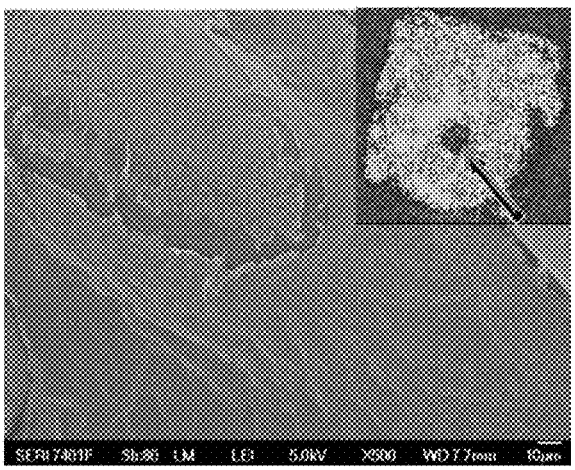
FIG. 5B shows bioluminescent images of infected mesh after treatment, with a central clearing (indicated using an arrow) where biofilm has been eradicated.
Figure 5B:
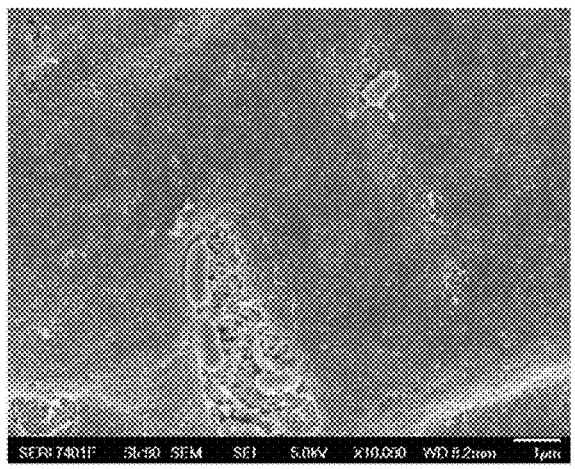

Referring to FIGS. 5A and 5B, Survival of *Pseudomonas aeruginosa* was detected using bioluminescent imaging. The bioluminescent imaging system (Hamamatsu Photonics KK, Bridgewater, N.J.) included an intensified charge-coupled-device camera mounted in a light-tight specimen chamber fitted with a light-emitting diode. In the photon-counting mode, an image of the light emitted from the bacteria is captured by using an integration time of two minutes at a maximum setting on the image-intensifier control module. Through the use of ARGUS software (Hamamatsu), the luminescent image is presented as a false-color image superimposed on a grayscale reference image. The image-processing component of the software calculates the total pixel valves (in Relative Luminescence Units (RLU)) of the infected mesh area. Imaging was performed before treatment with PEF, and immediately after treatment. The percentage of eradicated bacteria can be determined by the intensity of the bioluminescent images. The correlation between bioluminescence and bacterial eradication involves correlating the colony-forming units (CFU) and RLU in agar plates in dark control and after treatment with photodynamic therapy.

As further evaluation and confirmation of the disruption of biofilms, sterile uninfected mesh, untreated infected mesh, and treated infected mesh were processed for Scanning Electron Microscopy (SEM). Samples were placed in one-half (½) strength Karnovsky's fixative immediately after treatment and imaging. Samples remained in fixative for twenty-four hours prior to embedding. After fixing the samples for twenty-four hours, they were dehydrated in a series of graded ethanol concentrations. A Tousimis Samdri semi automatic Critical Point Dryer was used to completely dehydrate the samples. The mesh was then mounted on aluminum stubs and coated with Chromium with a GATAN 610 Ion Beam Coater. Samples were then viewed in the SEM at a voltage of 5 kV. For image scanning a JEOL 7401F Field Emission Scanning Electron Microscope was used. Magnification of images ranged from 25× to 10000×. One to three fields were obtained at each magnification.

For data analysis, a method of determining critical electroporation parameters was used. A set of images before and after the treatment were used to derive the parameters. First, the luminescence intensity was normalized to the correct value to compensate for the difference in the microscope settings before and after the scanning. Following the normalization, the pixels were converted to distances, where each pixel length was 5 mm. The intensity as a function of radius r, for each exposure time t, $I_t(r)$ was obtained by calculating the average intensity of a cluster of bacteria according to the following:

$$I_t(r) = \frac{1}{N_r} \sum_{r-\delta \leq r \leq r+\delta} I_t(r) \quad (2)$$

where $r = \sqrt{(x-x_{ct})^2 + (y-y_{ct})^2}$ represents the spherical radius from the center of the plate $(x_{ct}, y_{ct})$; (x, y) are the coordinates of the plate; δ is the length of the cluster in mm, and $N_r$ is the normalization factor, which refers to the number of pixels in the cluster in the spherical radius. The intensity over different distances, $I_t(r)$, was converted to intensity over electrical field strength using Equation (1).

The relationship between the survival fraction and the treatment time (for a predetermined pulse energy) is commonly described by a mathematical model based on the Weibull distribution:

$$\log S = -\frac{1}{2.303}\left(\frac{E}{b}\right)^n \quad (3)$$

where S is the survival fraction of bacteria after the treatment, E is the local electric field, and b and n are the field normalization and field exponent factors that can be estimated from fitting the empirical data for each pulse rate. The fitting used to estimate these parameters was least-squares nonlinear curve-fitting. The Weibull distribution depicts the dependence of bacterial survival on electric field intensity. A medium-scale Quasi-Newton line search for the fitting algorithm was used.

To quantify the effect of pulse number using 100, 150, and 300 pulses, where the voltage, pulse length duration, and frequency remained unchanged (1500V, 50 µs, and 2 Hz, respectively), the images before and after treatment with concentric ring electrodes were analyzed. The effect of treatment was measured as a function of the radius of central clearing as seen in the bioluminescent images of the mesh. In images of the mesh before and after treatment with concentric ring electrodes, it was seen that in all treatments with 150 and 300 pulses there was an effect that resulted in lower intensity in the images after treatment. To quantify the treatment effect, areas with over 80% eradication were deemed to be effective eradicated areas. According to this criterion, the critical electrical field strength was 121±14 V/mm when 300 pulses were applied, 235±6.1 V/mm when 150 pulses were applied, with related eradication area of 50.5±9.9 mm$^2$ for 300 pulses and 13.4±0.65 mm$^2$ for 150 pulses (see Table 1, showing bacterial eradication results for number of pulses delivered, in which V1=1500, V2=0, 50 µs pulse length duration, and 2 Hz).

TABLE 1

| Treatment | $E_{cr}$ for 80% Eradication (V/mm) | Area Eradicated over 80% (mm$^2$) |
|---|---|---|
| 100 pulses | none | none |
| 150 pulses | 121 ± 14 | 50.5 ± 9.9 |
| 300 pulses | 235 ± 6.1 | 13.4 ± 0.65 |

This indicates that the treatment efficacy increases as the number of pulses increases. A clear increase in treatment efficacy is appreciated at the center of the mesh, which was the area that received the strongest electric field delivery even at 100 pulses. A thick biofilm matrix (see FIG. 5A left) wedged into interstices was noted in control untreated infected mesh. Dense bacteria were present with a clear production of exopolysaccharide (see FIG. 5A right), which is associated with biofilm formation. After treatment with PEF even with 100 pulses, the biofilm was disrupted and a layer of debris was left behind at the center of the ring (see FIG. 5B left), where the fields where the highest. The few remaining scant rods (see FIG. 5B right) displayed abnormal morphology and exopolysaccharide was not visible. The mesh was not damaged by PEF treatment.

Figure 6A:
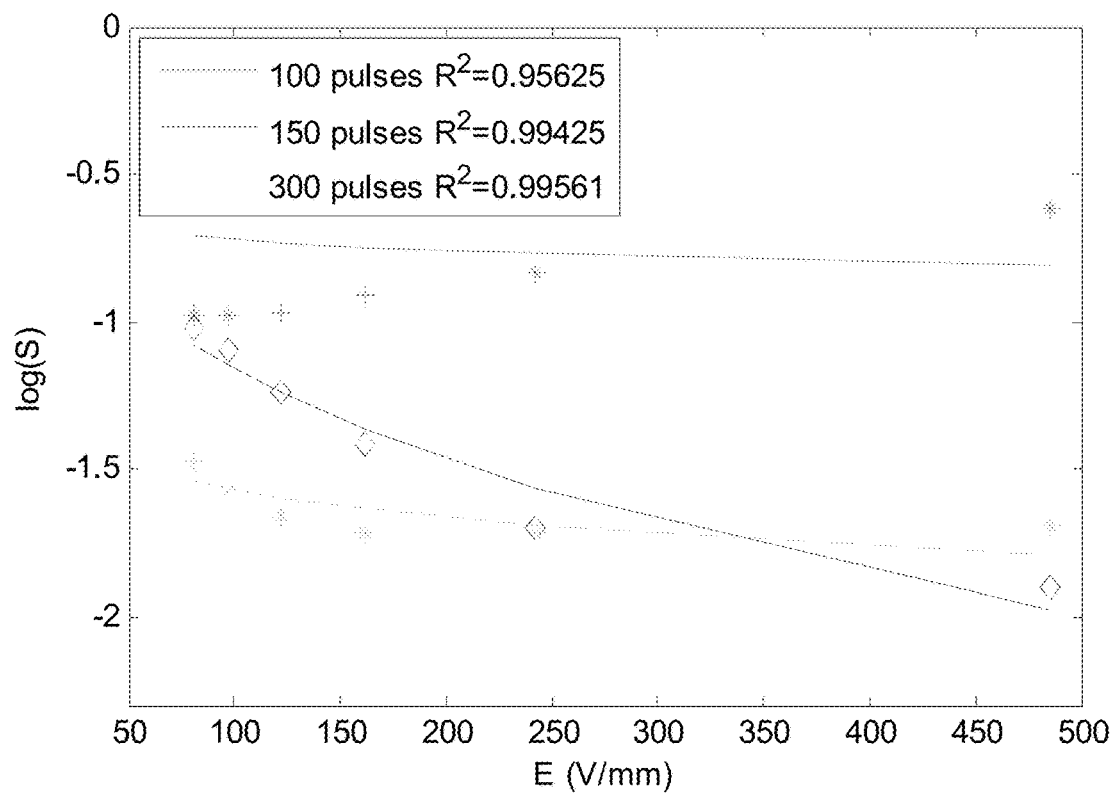
FIGS. 6A and 6B show Log(Survival Ratio) of bacteria per treatment group.
Figure 6B:
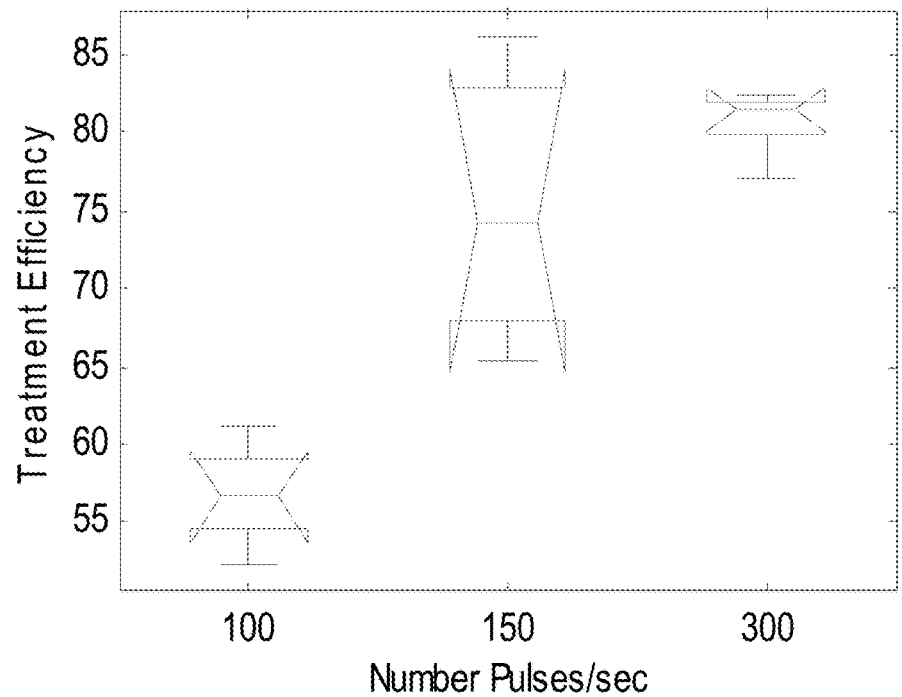

Survival rate is defined as the ratio of bacterial survival (measured as RLU) compared to the initial value, and is depicted in a logarithmic scale. FIG. 6A shows the average of all treatments per pulse group, compared to the theoretical Weibull distribution as a function of the electrical field strength. It can be appreciated from the figure that the survival rate decreases as the number of pulses and electrical field strength increase. However, at the lower pulse rate of 100 pulses, the effect of the treatment is similar across different electrical field strengths; whereas, at the higher pulse rate of 300 pulses, there is a more dramatic effect at the center of the mesh, where the electrical field strength is highest. An ANOVA test (FIG. 6B) shows that the p-value between the different conditions (pulse number) is $5.6 \times 10^{-5}$ with error degrees of freedom (df) of 15, which indicates that the increased efficacy of treatment is due to the increased number of pulses delivered. The average values between the conditions were 57.41, 74.35, and 81.11, for the 50, 150, and 300 number of initial pulses, respectively. A multiple comparisons testing (pairwise comparison) using "Tukey-Kramer" criterion that was performed after the ANOVA, showed that the difference between the estimated group means can be seen from FIG. 6B. The differences in means between 150 and 300 pulses is −6.7579, which is significantly lower than the one between 150 and 50, and 300 and 50 (−16.9356, and −23.6935, respectively). Still, the lower and upper limits for 95% confidence intervals for 150 and 300 pulses were −12.2820 and −1.2338, respectively, with p-value of 0.101, which indicates a marginal significance between 150 and 300 pulses. This indicates that the effect of number of pulses between 150 and 300 pulses is considerably small compared to lower pulse numbers. Table 1 (above) summarizes the treatment efficacy of each of the three groups of pulses.

In comparing the treatment efficacy to a theoretical model, the model fitting to the theoretical Weibull distribution in Equation (3) is very high with a correlation coefficient R2 of 0.9563, 0.9943, and 0.9956, for the 100, 150, and 300 pulses, respectively. The model fitting is more accurate in the case of higher pulses, where the treatment effect is more significant. The model fitting parameters used, and their corresponding R2, are depicted in Table 2.

TABLE 2

| Treatment | (b, n) | R$^2$ |
|---|---|---|
| 100 pulses | −0.49, 0.074 | 0.9563 |
| 150 pulses | 5.4650, 0.3379 | 0.9943 |
| 300 pulses | 0.0001, 0.0828 | 0.9956 |

These experiments demonstrated that pulsed electric fields can eradicate bacteria and disrupt biofilms in mesh implants without damaging the mesh. The results demonstrate the effectiveness of PEF treatment of biofilm-infected mesh, showing increased bacterial eradication with increased number of pulses, and with increased electrical field strength. Additionally, the area of complete eradication of bacteria increases as the number of pulses increases (p=0.000056). This indicates that increased efficacy of treatment is due to increased number of pulses delivered. Additionally, the p-value between the conditions of 150 and 300 pulses was 0.101, which indicates a marginal significance between 150 and 300 pulses. This indicates that the effect of number of pulses between 150 and 300 pulses is considerably small compared to lower pulse numbers (50), where the effect on survival rate is less. This suggests that protocols with fewer than 300 pulses may be suitable, without significant impact on treatment efficiency. Suitable protocols for other biofilms, devices, and applications can be determined and evaluated using techniques similar to those used for synthetic mesh infected with *Pseudomonas aeruginosa*, or using other techniques and approaches where appropriate.

The protocols selected—i.e., the depth of PEF treatment—can be controlled in order to avoid damage to surrounding tissue and/or organs if clinically applied in a patient with infected mesh. The treated area in the clinical scenario will be predefined by the configuration of the electrodes and the applied PEF parameters. In order for the effect of PEF treatment to be maximized, it would work synergistically with the human immune system and intravenous (IV) antibiotics. PEF could be used to stimulate the immune system by recruiting inflammatory cytokines and mediators to the site of treatment, and it has the potential to eradicate the biofilm synergistically with antibiotics. Disruption of bacteria in the biofilm could decrease the concentration of secreted molecules such as eDNA in the biofilm, therefore enabling more efficient drug delivery to the treated area.

PEF treatment mitigates the problem of antibiotic resistance. Additionally, PEF does not involve enzymatic removal, chemical treatments, metallic nanoparticles, chelating agents, or other methods previously applied to biofilms. Moreover, PEF is a non-thermal treatment that is not expected to destroy the integrity of medical devices (such as the mesh, which is not damaged), while sparing surrounding tissue from injury. Combining antibiotic therapy with PEF could effectively eradicate biofilms, therefore avoiding mesh removal and/or life-long high dose antibiotic therapy. The disinfection system 100 could be customized with an array of needles at various distances apart from each other to treat any given infected device in a patient.

The present invention has been described in terms of one or more preferred embodiments, and it should be appreciated that many equivalents, alternatives, variations, additions, and modifications, aside from those expressly stated, and apart from combining the different features of the foregoing versions in varying ways, can be made and are within the scope of the invention. It should be appreciated that the invention is applicable to other procedures and to achieve other objectives as well. Following are additional examples. These examples are not to be construed as describing the only additions and modifications to the invention. It is expressly contemplated that any of the processes or steps described herein may be combined, eliminated, or reordered. Accordingly, this description is meant to be taken only by way of example, and not to otherwise limit the scope of this invention. The patentable scope of the invention is defined by the claims and may include other examples that occur to those skilled in the art.

For example, although protocols were discussed with respect to eradiation of an infection on a mesh, the features and advantages that arise due to the invention are well suited to other implants as well as other devices generally (medical or otherwise). Additionally, it should be appreciated that the above systems and methods can be implemented using hardware, software, single integrated devices, multiple devices in wired or wireless communication, or any combination thereof.

What is claimed is:

1. A method for disinfecting a medical device using pulsed electric fields, the method including the steps of:
    a. identifying one or more characteristics of a microbial biofilm to be eradicated, the biofilm being located on or in a medical device;
    b. selecting a suitable protocol for the pulsed electric field to be applied, the selected protocol defining:
       1) a voltage; and
       2) a pulse frequency;
    c. positioning an electrode system at a medical device to be disinfected;
    d. applying a pulsed electric field to the microbial biofilm to eradicate at least a portion of the microbes in the biofilm, the pulsed electric field having:
       1) A voltage of at least 1000 volts;
       2) An electric field strength of at least 150 V/mm; and
       3) a pulse frequency of at least 1 Hz.

2. The method of claim 1, wherein the medical device is a synthetic mesh, the method further including the step of diagnosing a mesh infection.

3. The method of claim 1, further including the step of using a systemic antimicrobial in combination with the pulsed electric field.

4. The method of claim 1, further including the steps of inserting the electrode system in a patient and positioning the electrode system at an implanted medical device to be disinfected.

5. The method of claim 1, wherein the selected protocol further defines:
    1) A number of pulses; and
    2) a pulse duration.

6. The method of claim 5, wherein the number of pulses is at least 150 pulses and wherein the pulse duration is at least 25 µs.

7. The method of claim 1, wherein selecting a suitable protocol for the pulsed electric field to be applied further comprises:
    selecting a suitable protocol for the pulsed electric field to be applied based on the one or more characteristics of the microbial biofilm, and
    wherein applying a pulsed electric field to the microbial biofilm to eradicate at least a portion of the microbes in the biofilm further comprises:
    applying a pulsed electric field to the microbial biofilm to eradicate at least a portion of the microbes in the biofilm based on the selected protocol.

* * * * *